US006172276B1

United States Patent
Hetzler et al.

(10) Patent No.: US 6,172,276 B1
(45) Date of Patent: Jan. 9, 2001

(54) STABILIZED ABSORBENT MATERIAL FOR IMPROVED DISTRIBUTION PERFORMANCE WITH VISCO-ELASTIC FLUIDS

(75) Inventors: Connie Lynn Hetzler, Sparta, NJ (US); Nancy Donaldson Kollin, Roswell, GA (US); Crystal Sutphin Leach, Atlanta, GA (US); Jack Nelson Lindon, Alpharetta, GA (US); Lawrence Howell Sawyer, Neenah, WI (US); Heather Anne Sorebo, Appleton, WI (US); Garry Roland Woltman, Greenville, WI (US)

(73) Assignee: Kimberly-Clark Worldwide, Inc., Neenah, WI (US)

( * ) Notice: Under 35 U.S.C. 154(b), the term of this patent shall be extended for 0 days.

(21) Appl. No.: 09/047,778

(22) Filed: Mar. 25, 1998

Related U.S. Application Data (60) Provisional application No. 60/046,480, filed on May 14, 1997.

(51) Int. Cl.$^7$ .................................................. A61F 13/15
(52) U.S. Cl. .................... 604/378; 604/385.01; 604/358
(58) Field of Search .............................. 604/385.01, 358, 604/378

(56) References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 4,340,563 | 7/1982 | Appel et al. | 264/518 |
| 5,037,409 | 8/1991 | Chen et al. | 604/358 |
| 5,057,368 | 10/1991 | Largman et al. | 428/397 |
| 5,069,970 | 12/1991 | Largman et al. | 428/373 |
| 5,108,820 | 4/1992 | Kaneko et al. | 428/198 |
| 5,108,827 | 4/1992 | Gessner | 428/219 |
| 5,200,248 | 4/1993 | Thompson et al. | 428/131 |
| 5,277,976 | 1/1994 | Hogle et al. | 428/397 |
| 5,336,552 | 8/1994 | Strack et al. | 428/224 |
| 5,382,400 | 1/1995 | Pike et al. | 264/168 |
| 5,466,232 | 11/1995 | Cadieux et al. | 604/378 |
| 5,466,410 | 11/1995 | Hills | 264/172.11 |
| 5,549,589 | 8/1996 | Horney et al. | 604/366 |

FOREIGN PATENT DOCUMENTS

| | | | |
|---|---|---|---|
| 0 359 501 | 3/1990 | (EP) | A61F/13/15 |
| 0 494 112 | 7/1992 | (EP) | A61F/13/15 |
| 0 523 683 | 1/1993 | (EP) | A61F/13/46 |
| 94/26221 | 11/1994 | (WO) | A61F/13/46 |
| 95/17867 | 7/1995 | (WO) | A61F/13/00 |
| 95/17870 | 7/1995 | (WO) | A61F/13/15 |
| 96/19171 | 6/1996 | (WO) | A61F/13/15 |
| 96/40513 | 12/1996 | (WO) | B32B/27/12 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

Burgeni and Kapur, The Textile Research Journal, vol. 37(1967), p. 356.

Chatterjee's Absorbency, Elsevier Science Publishers, B.V. 1985, pp. 36–40.

*Primary Examiner*—John G. Weiss
*Assistant Examiner*—Paul Shanoski
(74) *Attorney, Agent, or Firm*—James B. Robinson (57) ABSTRACT

There is provided a distribution material for personal care products which is a fabric which wicks artificial menses according to a horizontal wicking test a distance of about 1 inch in less than about 1.5 minutes. Materials meeting this performance criteria generally have a pore size distribution with a high percentage (usually more than 50 percent) of pore diameters between about 80 and 400 microns and a density below about 0.15 g/cc.

7 Claims, 7 Drawing Sheets

STABILIZED ABSORBENT MATERIAL FOR IMPROVED DISTRIBUTION PERFORMANCE WITH VISCO-ELASTIC FLUIDS

This application claims priority from U.S. Provisional Application No. 60/046,480 filed May 14, 1997.

FIELD OF THE INVENTION

The present invention relates to a material structure in an absorbent article for personal care products like sanitary napkins.

BACKGROUND OF THE INVENTION

Performance objectives for sanitary napkins or pads include a dry feeling for the wearer, comfort due to appropriate fit throughout the life of the pad, and low leakage from the product.

Most commercially available pads have relatively high leakage rates. These pads may fail as much as 30 percent of the time, and failure rates of about 20 percent are quite common. Such failures are believed to be due to the highly viscous nature of menses and the great variability in delivery volume which results in overloading of the pad in the target area and subsequent leaking. Insufficient distribution of menses is believed to be one of the key causes of the target area overloading.

In the field of urine management in personal care products like diapers, distribution is often provided by materials that have small pores with a narrow pore size distribution.

These materials must move the high volume, low viscosity urine insults out of the target area in a time sufficient for the target area to be able to accept the next insult. The movement of urine may be to relatively remote parts of the diaper overcoming substantial hydrostatic pressure. In contrast, feminine hygiene products experience lower total insult volume but the fluid is of greater viscosity, making it more difficult to move the fluid. Distribution materials must be quite different for feminine hygiene products than for products concerned primarily with urine management.

Previous attempts to provide lower leakage feminine hygiene products include U.S. Pat. Nos. 5,549,589, 5,466,232 and 5,200,248, which discuss distribution structures for menses. None of these references provide the unique combination of attributes of the instant invention.

It is an object of this invention to provide a feminine hygiene products having superior distribution performance to allow movement of menses from the target area and provide comfort, dry feeling, and lower leakage than traditional pads.

SUMMARY OF THE INVENTION

The object of the invention is achieved by a distribution material comprised of stabilized, highly wettable fibers arranged to provide capillary pore sizes and a degree of wettability ideally suited to wick visco-elastic fluids. When exposed to a visco-elastic fluid and simulants, these materials demonstrate improved fluid distribution performance in terms of the distance wicked, the wicking rate, as well as the amount of fluid moved.

The distribution material for personal care products of this invention is a fabric which wicks artificial menses according to a horizontal wicking test a distance of about 1 inch in less than about 1.5 minutes. Materials meeting this performance criteria generally have a pore size distribution with a high percentage (usually more than about 50 percent) of pore diameters between about 80 and 400 microns and a density below about 0.15 g/cc.

DEFINITIONS

"Disposable" includes being disposed of after use and not intended to be washed and reused.

"Front" and "back" are used throughout this description to designate relationships relative to the garment itself, rather than to suggest any position the garment assumes when it is positioned on a wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic.

"Inward" and "outward" refer to positions relative to the center of an absorbent garment, and particularly transversely and/or longitudinally closer to or away from the longitudinal and transverse center of the absorbent garment.

"Layer" when used in the singular can have the dual meaning of a single element or a plurality of elements.

"Liquid" means a substance and/or material that flows and can assume the interior shape of a container into which it is poured or placed.

"Liquid communication" means that liquid is able to travel from one layer to another layer, or one location to another within a layer.

"Longitudinal" and "transverse" have their customary meaning. The longitudinal axis lies in the plane of the article when laid flat and fully extended and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Particles" refers to any geometric form such as, but not limited to, spherical grains, cylindrical fibers or strands, flat surfaces or roughened surfaces, sheets, ribbons, strings, strands, or the like.

"Spray" and variations thereof include forcefully ejecting liquid, either as a stream or, such as swirl filaments, or atomized particles through an orifice, nozzle, or the like, by means of an applied pressure of air or other gas, by force of gravity, or by centrifugal force. The spray can be continuous or non-continuous.

"Spunbonded fibers" refers to small diameter fibers which are formed by extruding molten thermoplastic material as filaments from a plurality of fine, usually circular, capillaries of a spinneret with the diameter of the extruded filaments then being rapidly reduced as by, for example, the process described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 30 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

"Conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. Nos. 5,277,976 to Hogle et al., and 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Bonded carded web" refers to webs which are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

"Personal care product" means diapers, training pants, absorbent underpants, adult incontinence products, bandages and feminine hygiene products.

"Feminine hygiene products" means sanitary napkins or pads.

"Target area" refers to the area or position on a personal care product where an insult is normally delivered by a wearer.

TEST METHODS

Material caliper (thickness)

The caliper of a material is a measure of thickness and is measured at 0.05 psi with a Starret-type bulk tester, in units of millimeters.

Density

The density of the materials is calculated by dividing the weight per unit area of a sample in grams per square meter (gsm) by the bulk of the sample in millimeters (mm) at 68.9 Pascals and multiplying the result by 0.001 to convert the value to grams per cubic centimeter (gtcc). A total of three samples would be evaluated and averaged for the density values.

Wicking Time and Horizontal Liquid Flux of an Absorbent Structure

A sample strip of material approximately 1 inch (2.5 cm) by 8 inches (20 cm) is placed horizontally such that when the sample strip is positioned in a liquid reservoir at the beginning of the test, the sample strip will just touch the liquid surface. The relative humidity should be maintained at about 90 to about 98 percent during the evaluation. The sample strip is placed next to an large (effectively infinite) amount of liquid and a stopwatch started as soon as the edge of the sample strip touches the surface of the solution.

The horizontal distance of the liquid front traveling along the sample strip and the liquid weight absorbed by the sample strip at various times is recorded. The weight of the liquid absorbed by the sample strip from the beginning of the evaluation to about a half inch (1.3 cm), 1 inch, 2 inches (5 cm) and 3 inches (7.6 cm) is also determined from the data.

The liquid used in this testing was a fluid designed to simulate the visco-elastic and other properties of menses. In order to prepare the fluid, blood, in this case defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well.

Eggs, in this case jumbo chicken eggs, were separated, the yolk and chalazae discarded and the egg white retained. The egg white was separated into thick and thin portions by straining the white through a 1000 micron nylon mesh for about 3 minutes, and the thinner portion discarded. Note that alternative mesh sizes may be used and the time or method may be varied provided the viscosity is at least that required. The thick portion of egg white which was retained on the mesh was collected and drawn into a 60 cc syringe which was then placed on a programmable syringe pump and homogenized by expelling and refilling the contents five times. In this example, the amount of homogenization was controlled by the syringe pump rate of about 100 ml/min, and the tubing inside diameter of about 0.12 inches. After homogenizing the thick egg white had a viscosity of about 20 centipoise at 150 $sec^{-1}$ and it was then placed in the centrifuge and spun to remove debris and air bubbles at about 3000 rpm for about 10 minutes, though any effective method to remove debris and bubbles may be used.

After centrifuging, the thick, homogenized egg white, which contains ovamucin, was added to a 300 cc Fenwal® Transfer pack using a syringe. Then 60 cc of the swine plasma was added to the transfer pack. The transfer pack was clamped, all air bubbles removed, and placed in a Stomacher lab blender where it was blended at normal (or medium) speed for about 2 minutes. The transfer pack was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of this artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567, (717) 336-1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

Pore size distribution

The pore size distribution of a material is measured by using an apparatus based on the porous plate method used by Burgeni and Kapur in The Textile Research Journal, volume 37(1967), at p. 356. Using this apparatus, the amount of fluid desorbed from the sample material at various pressures can be correlated to the radius of the pores within the given material. This process is described in Chattterjee's Absorbency, Elsevier Science Publishers, B.V. 1985, pp. 36–40.

The modified system used consists of a movable stage interfaced with a programmable stepper motor and an electronic balance controlled by a personal computer. The control program automatically moves the stage to the desired height, collects data at a specified sampling rate until equilibrium is reached, and then moves to the next calculated height. A Plexiglas® support structure is used to maintain the material/porous plate in a level, upright position throughout the entire test. Controllable parameters of the method include sampling rates, criteria for equilibrium, and pore size range measured. Data for these tested materials were collected using mineral oil (o.82 g/cc, 32 dyne-cm, 0° fluid contact angle) as the test fluid. At the beginning of each test the sample material is placed on the porous plate and then the sample is completely saturated by lowering the porous plate structure. Pore size is then determined by gathering mass data as the pressure (i.e. height of the stage) increases. Equilibrium is established if after 4 intervals of 60 seconds, there was less than 0.05 grams/min change.

Date is presented as percent pore volume vs. pore radius in microns by plotting the pore size on the x-axis and the incremental change in mass divided by the overall change in mass on the y-axis.

DETAILED DESCRIPTION OF THE INVENTION

This invention is a class of distribution materials composed of stabilized, highly wettable fibers arranged to provide capillary pore sizes and a degree of wettability ideally suited to wick visco-elastic fluids. When exposed to a visco-elastic fluid or fluid simulant, these materials demonstrate improved fluid distribution performance for distance wicked, wicking rate and amount of fluid moved. The pore characteristics are stable whether dry or wet with minimal, preferably less than about 25 percent, more particulary 20 percent and still more particularly 15 percent, swelling or collapse when wetted with the visco-elastic fluid simulant. All of these properties are critical to the overall performance of distribution materials placed in the target area of personal care products like feminine pads.

The caliper (in inches) of the materials measured in a dry state and wet, i.e., after saturation with the menses simulant, using a compressometer at 0.02 psi with a 2 inch diameter foot are shown below:

| Basis weight (gms) | Density (g/cc) | Pulp/binder Percentage | | Dry Caliper | Wet Caliper | Collapse |
|---|---|---|---|---|---|---|
| 100 | 0.06 | 90/10 | | 0.075 | 0.069 | 0.006 |
| | | | | 0.077 | 0.065 | 0.012 |
| | | | | 0.078 | 0.067 | 0.011 |
| | | | avg. | 0.077 | 0.067 | 0.010 |
| 100 | 0.10 | 90/10 | | 0.059 | 0.054 | 0.005 |
| | | | | 0.062 | 0.060 | 0.002 |
| | | | | 0.064 | 0.056 | 0.008 |
| | | | avg. | 0.062 | 0.057 | 0.005 |
| 200 | 0.08 | 90/10 | | 0.109 | 0.091 | 0.018 |
| | | | | 0.110 | 0.098 | 0.012 |
| | | | | 0.103 | 0.095 | 0.008 |
| | | | avg. | 0.107 | 0.095 | 0.013 |
| 200 | 0.20 | 90/10 | | 0.046 | 0.052 | -.006 |
| | | | | 0.050 | 0.047 | 0.003 |
| | | | | 0.042 | 0.044 | -.002 |
| | | | avg. | 0.046 | 0.048 | -.002 |

Fluid distribution capability requires the appropriate capillary pore structure within a specified range of weftability for the fluid of interest. Distribution materials were developed using several technology approaches that demonstrate the underlying material characteristics needed for favorable performance. Examples of such materials follow.

EXAMPLE 1

In this example, the distribution material consists of about 80 weight percent fluff pulp (Rayonier R-9401 mercerized southern softwood roll pulp) and about 20 weight percent Danaklon short cut (5 mm) 2.2 denier polyethylene/polypropylene (PE/PP) sheath/core conjugate binder fiber with an S2/B2/39 finish. This finish is advertised as remaining hydrophilic after repeated insults. The material was produced at three different densities; 0.05 g/cc, 0.1 g/cc and 0.2 g/cc at a basis weights of about 100 to 250 gsm. Examples of 0.05 g/cc, 0.1 g/cc and 0.2 g/cc materials at a basis weight of about 125 gsm are shown for comparison.

The materials were tested according to the Horizontal Wicking Test which was repeated for a total of three tests using 1 inch by 8 inch samples. Table 1 shows the results where weight is given in grams of retained fluid, time in seconds and DNR means did not reach.

The fluff pulp was from Rayonier Inc. of Jessup, Ga. 31545. The binder fibers were from Danaklon a/s, located at Engdraget 22, KD-6800 Varde, Denmark, and were 2.2 denier conjugate PE/PP sheath/core fibers cut into 5 mm lengths.

The distribution material was produced by the Dan-Web airlaying process. Any other satisfactory procedure known to those skilled in art may be used to produce the material. Some of the samples were tested for pore volume distribution. The results are shown graphically in FIGS. 1, 2, 3 and 4 which show the pore volume distribution for the 0.05 g/cc repetition 1, repetition 2 and the 0.1 g/cc repetition 2. The results show that as density is lowered and pore size is increased, wicking performance is greatly improved.

| | | Rep 1 | | Rep 2 | | Rep 3 | |
|---|---|---|---|---|---|---|---|
| | (inches) | Wt. (g) | Time(s) | Wt. (g) | Time(s) | Wt. (g) | Time(s) |
| 0.05 g/cc | 0.5 | 1.26 | 50 | 1.15 | 50 | 1.13 | 54 |
| | 1.0 | 1.80 | 161 | 1.77 | 170 | 1.55 | 170 |
| | 2.0 | 1.56 | 633 | 1.71 | 611 | 1.48 | 714 |
| | 3.0 | 1.02 | DNR | 0.89 | DNR | 0.72 | DNR |
| 0.1 g/cc | 0.5 | 0.86 | 20 | 0.68 | 24 | 0.76 | 18 |
| | 1.0 | 1.14 | 155 | 1.07 | 123 | 1.03 | 139 |
| | 2.0 | 0.95 | 811 | 0.91 | 868 | 0.9 | 810 |
| | 3.0 | 0.32 | DNR | 0.16 | DNR | 0.23 | DNR |
| 0.2 g/cc | 0.5 | 0.79 | 56 | 0.83 | 43 | 0.73 | 56 |
| | 1.0 | 1.11 | 253 | 1.03 | 174 | 0.98 | 245 |
| | 2.0 | 0.62 | DNR | 0.96 | 1074 | 0.76 | DNR |
| | | 0.21 | DNR | | | | |

EXAMPLE 2

Figure 1:
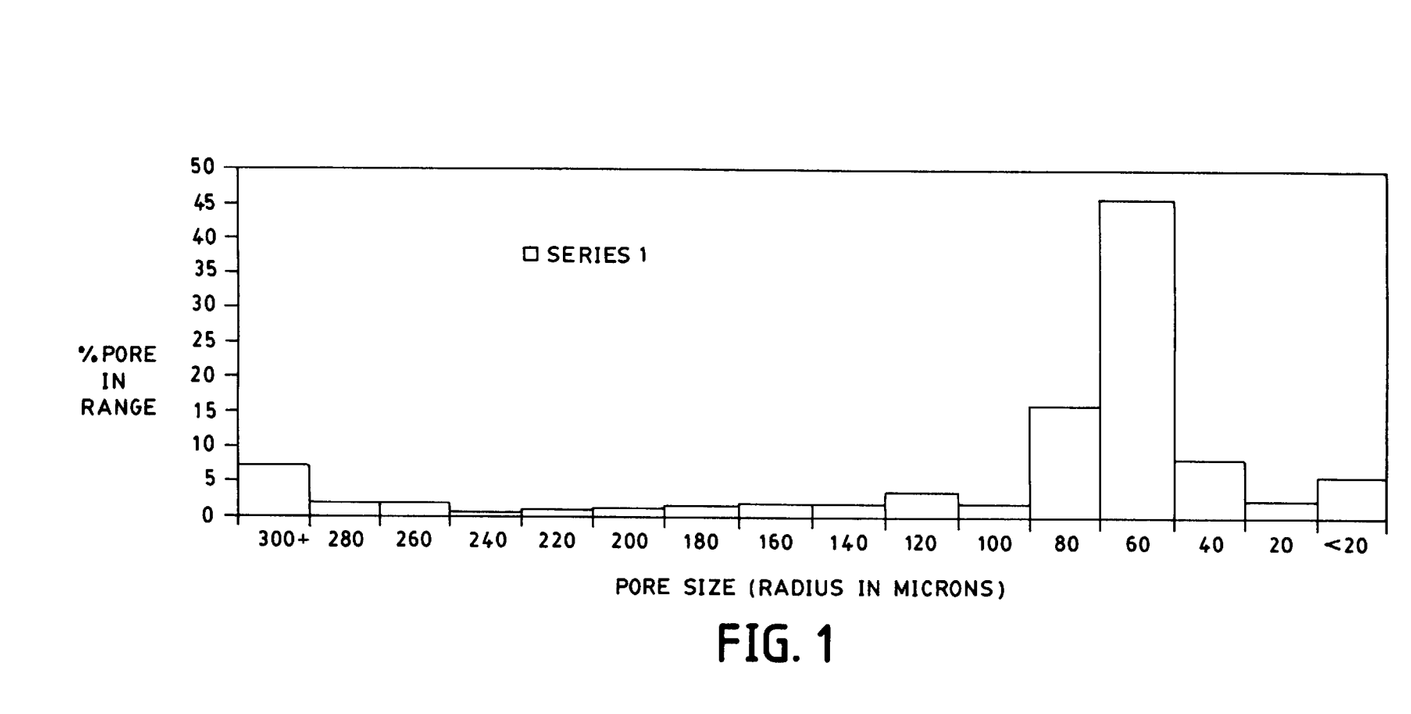
FIG. 1 is a graph of the pore size distribution of the 0.05 g/cc material of Example 1, repetition 1.
Figure 2:
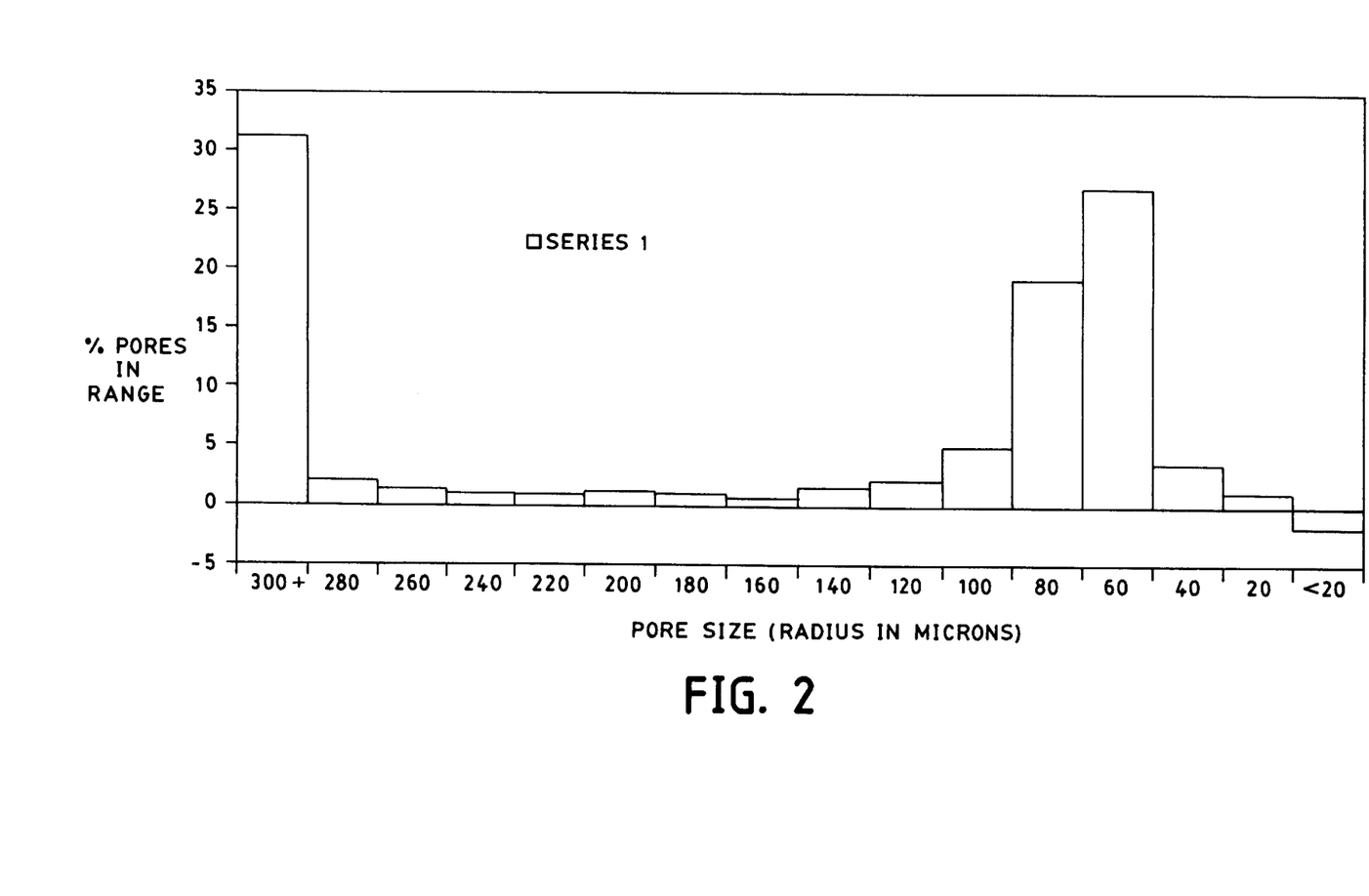
FIG. 2 is a graph of the pore size distribution of the 0.05 g/cc material of Example 1, repetition 2.
Figure 3:
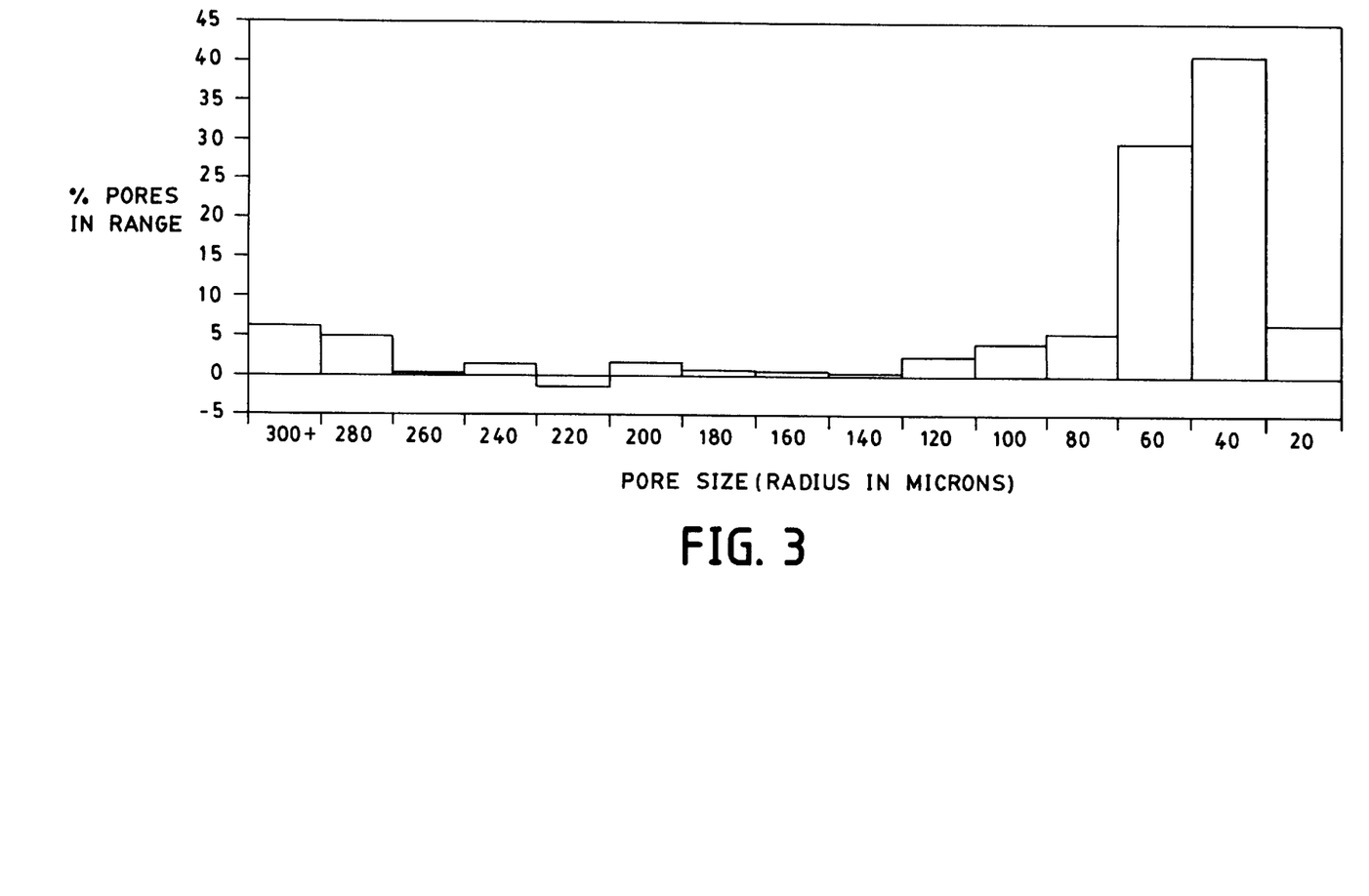
FIG. 3 is a graph of the pore size distribution of the 0.1 g/cc material of Example 1, repetition 1.
Figure 4:
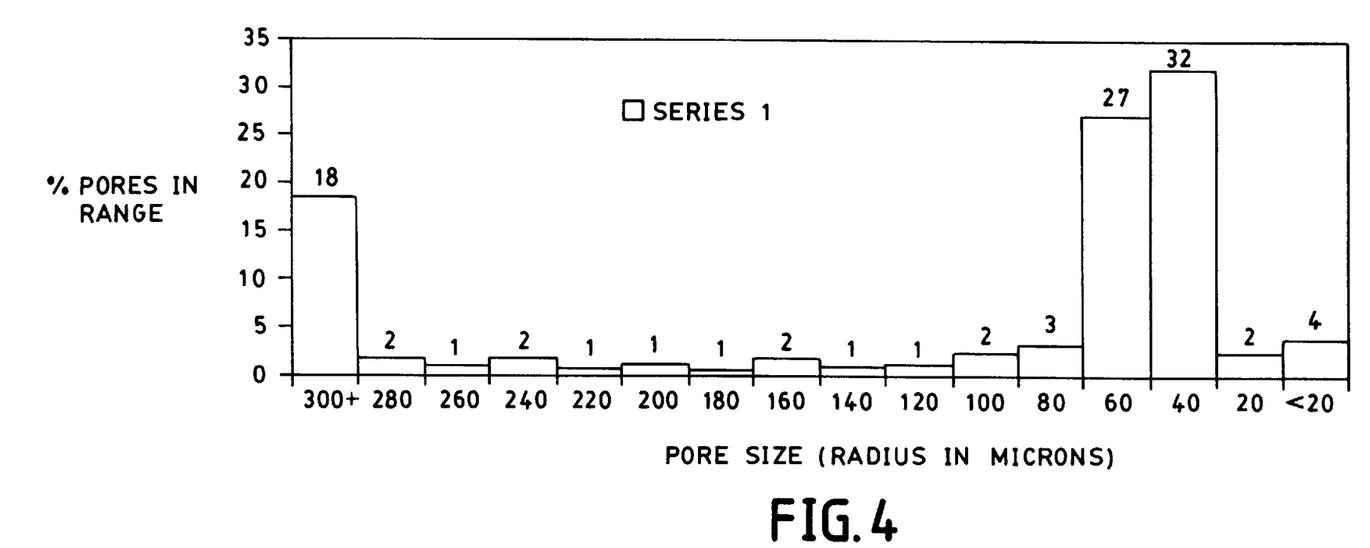
FIG. 4 is a graph of the pore size distribution of the 0.1 g/cc material of Example 1, repetition 2.
Figure 5:
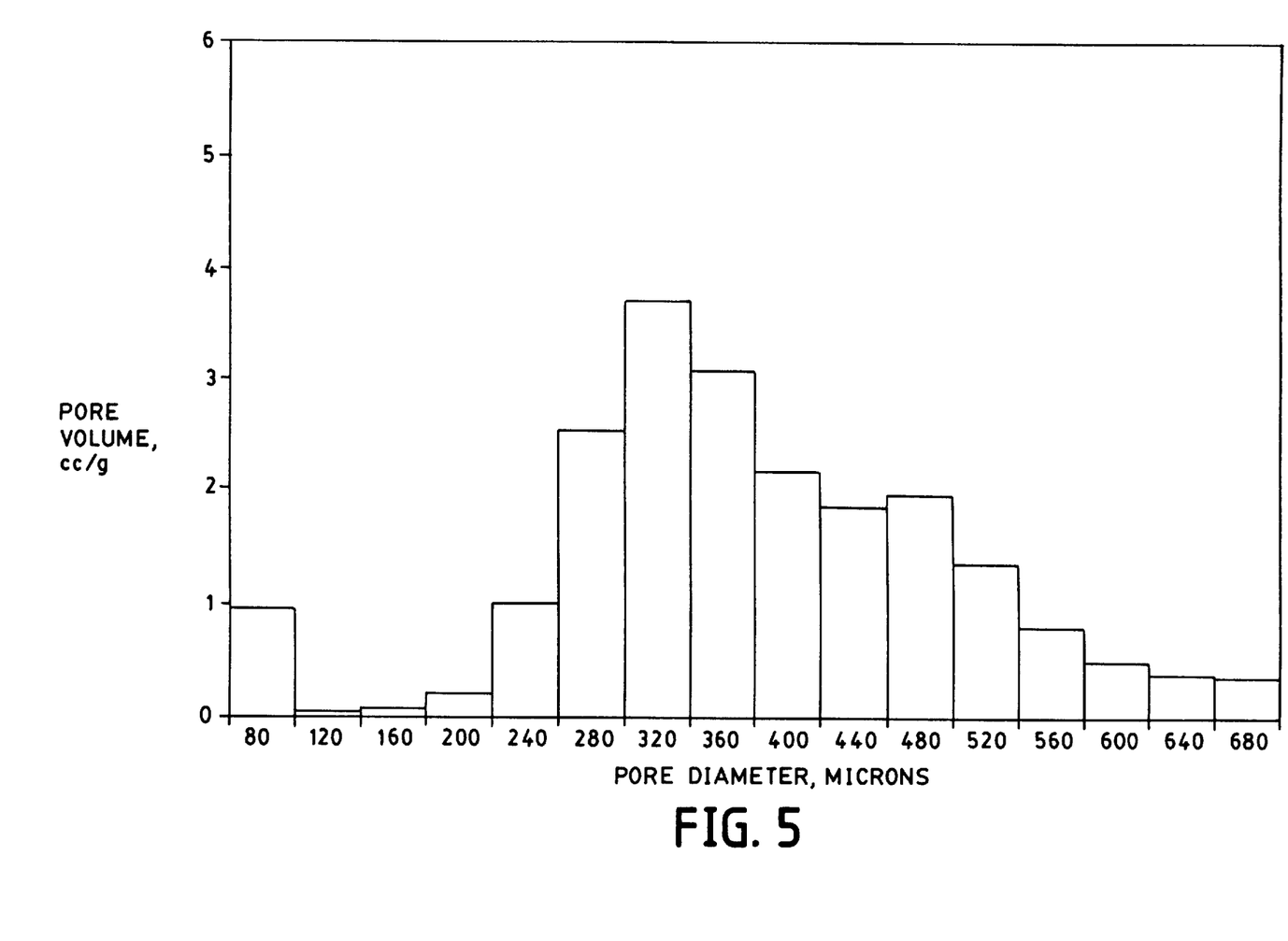
FIG. 5 is a graph of the pore size distribution of the unoriented 0.028 g/cc material of Example 2.
Figure 6:
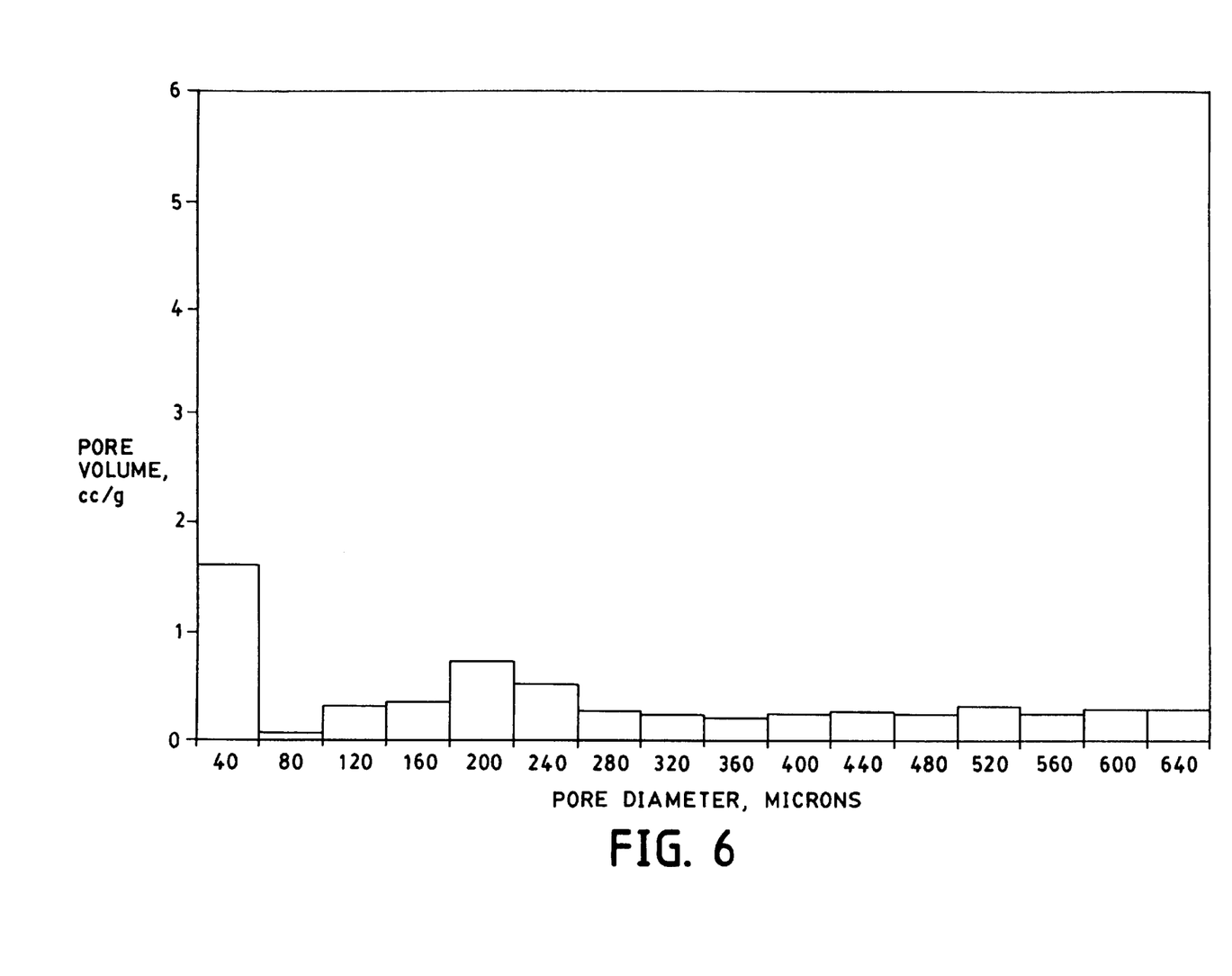
FIG. 6 is a graph of the pore size distribution of the 0.068 g/cc material of Example 2.
Figure 7:
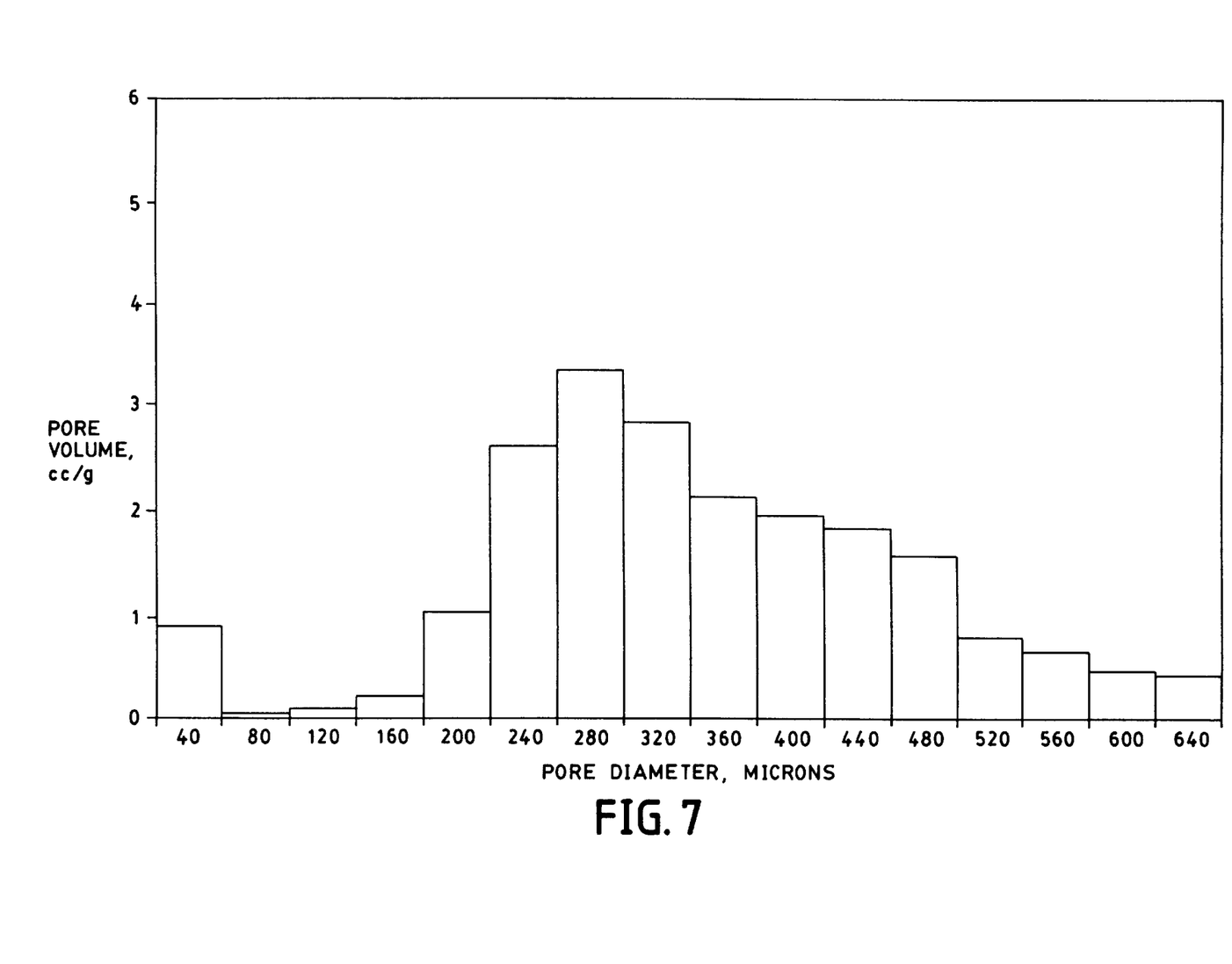
FIG. 7 is a graph of the pore size distribution of the oriented 0.028 g/cc material of Example 2.

In this example, the distribution materials are bonded carded webs consisting of 100 weight percent eccentric sheath/core conjugate fibers of polyethylene and polypropylene available from the Chisso Chemical Co. of Japan. The fibers had a finish known as HR6 applied to them. The table below shows the wicking results for a 0.028 g/cc sample, a 0.068 g/cc sample and a 0.028 g/cc sample in which the fibers were oriented in the carding process. In the table below, the distance is given in inches, the weight in grams and the time in minutes and seconds as indicated. The pore volume distribution was tested and the results are shown in FIGS. 5, 6 and 7 respectively. This data shows that when a high percentage of the pore volume has pores that range from about 200 to about 400 microns, better wicking results are achieved.

| Density | Distance | Weight | Time |
|---|---|---|---|
| 0.028 g/cc | 1.0 | 1.7 | 50 sec. |
| | 2.0 | 1.1 | 10 min. |
| | 3.0 | 0.9 | 17 min. |
| 0.068 g/cc | 1.0 | 0.6 | 1.5 min. |
| | 2.0 | 0.1 | DNR |
| 0.028 g/cc oriented | 1.0 | 1.7 | 1 min. |
| | 2.0 | 1.2 | 6.6 min. |
| | 3.0 | 0.9 | 18 min. |
| | 4.0 | 0.1 | 20+ min. |

The distribution material of this invention should wick the artificial menses fluid according to the horizontal wicking test a distance of an inch (2.5 cm) in less than about 1.5 minutes to be successful. Materials meeting this performance criteria generally have a pore size distribution with a high percentage (usually more than 50 percent, more particularly more than 60 percent and still more particularly more than 70 percent) of pore diameters between about 80 and 400 microns and a density below about 0.15 g/cc. Its believed that increasing the wettability of the pore surface results in greater wicking driving forces which can maintain liquid movement in smaller pores with higher resistive forces.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A distribution material for personal care products comprising a nonwoven fabric having a density of about 0.10 g/cc or less and having pore diameters wherein more than 50 percent of said pore diameters are between about 80 and 400 microns, wherein said distribution material wicks artificial menses according to a horizontal wicking test a distance of at least about 1 inch in less than about 3 minutes time from initial insult, at which 3 minute time said material holds at least 1 gm of said artificial menses.

2. The distribution material of claim 1 having pore diameters wherein more than 60 percent of said pore diameters are between about 80 and 400 microns.

3. The distribution material of claim 1 having pore diameters wherein more than 70 percent of said pore diameters are between about 80 and 400 microns.

4. A feminine hygiene sanitary napkin comprising a nonwoven distribution material made according to an airlaying process and having a density of less than about 0.15 g/cc and pore diameters wherein more than 50 percent of said pore diameters are between about 80 and 400 microns, wherein said distribution material wicks artificial menses according to a horizontal wicking test a distance of at least about 1 inch in less than about 3 minutes time from initial insult, at which 3 minute time said material holds at least 1 gm of said artificial menses.

5. The distribution material of claim 1 wherein said nonwoven fabric comprises conjugate fibers.

6. The distribution material of claim 1 wherein said nonwoven fabric comprises a mixture of fluff pulp fibers and conjugate fibers.

7. The distribution material of claim 1 wherein said nonwoven fabric is made according to a method selected from the group consisting of airlaying, and bonding and carding.

* * * * *